United States Patent
Cherpeck

(10) Patent No.: US 6,384,280 B1
(45) Date of Patent: May 7, 2002

(54) PROCESS FOR THE PREPARATION OF POLYALKYLPHENOXYAMINOALKANES

(75) Inventor: Richard E. Cherpeck, Cotati, CA (US)

(73) Assignee: Chevron Oronite Company LLC, San Ramon, CA (US)

(*) Notice: Subject to any disclaimer, the term of this patent is extended or adjusted under 35 U.S.C. 154(b) by 0 days.

(21) Appl. No.: 09/976,747

(22) Filed: Oct. 12, 2001

(51) Int. Cl.⁷ .............................................. C07C 217/00
(52) U.S. Cl. ...................................... 564/353; 564/354
(58) Field of Search ................................. 564/353, 354

(56) References Cited

U.S. PATENT DOCUMENTS

| | | | |
|---|---|---|---|
| 4,381,401 A | 4/1983 | Poindexter | 556/410 |
| 5,669,939 A | 9/1997 | Cherpeck | 44/425 |
| 5,851,242 A | 12/1998 | Cherpeck et al. | 44/425 |

FOREIGN PATENT DOCUMENTS

| DE | 19711004 A1 | 10/1997 |
|---|---|---|
| JP | 2592732 B2 | 3/1997 |

OTHER PUBLICATIONS

Martin E. Dyen and Daniel Swern, *Chemistry Reviews* (1967), pp. 197–246.

*Primary Examiner*—Samuel Barts
(74) *Attorney, Agent, or Firm*—Steven G. K. Lee

(57) ABSTRACT

A process for the preparation of polyalkylphenoxyaminoalkanes which comprises the aminoethylation of a polyalkylphenol compound in the presence of a basic catalyst with 2-oxazolidinone or a derivative thereof having the following formula:

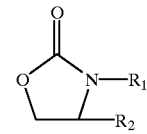

wherein $R_1$ and $R_2$ are independently hydrogen or lower alkyl having 1 to about 6 carbon atoms and wherein the polyalkyl group of said polyalkylphenol has an average molecular weight in the range of about 600 to 5,000.

23 Claims, No Drawings

PROCESS FOR THE PREPARATION OF POLYALKYLPHENOXYAMINOALKANES

FIELD OF THE INVENTION

The present invention relates to a process for the preparation of polyalkylphenoxyaminoalkanes. More particularly, this invention relates to a process for the preparation of polyalkylphenoxyaminoalkanes which comprises the aminoethylation of a polyalkylphenol compound with 2-oxazolidinone or a derivative thereof.

BACKGROUND OF THE INVENTION

Polyalkylphenoxyaminoalkanes are known fuel additives useful in the prevention and control of engine deposits. U.S. Pat. Nos. 5,669,939 and 5,851,242 describes a process for preparing these compounds. The process involves initially hydroxylating a polyalkylphenol with an alkylene carbonate in the presence of a catalytic amount of an alkali metal hydride or hydroxide, or alkali metal salt, to provide a polyalkylphenoxyalkanol which is subsequently reacted with an appropriate amine to provide the desired polyalkylphenoxyaminoalkane.

2-oxazolidinones or derivatives thereof are well described. For example, Martin E. Dyen and Daniel Swern, *Chemistry Reviews* (1967), pages 197–246 describes 2-oxazolidinones in detail. The use of 2-oxazolidinones or derivatives thereof in the aminoethylation of phenols is well known in the art.

U.S. Pat. No. 4,381,401 discloses the reaction of 2-oxazolidinone or N-substituted derivatives thereof with aromatic amine hydrochlorides at elevated temperatures to produce 1,2-ethanediamines. The 1,2-ethanediamines produced are an important class of materials which are useful as intermediates for the production of pharmaceuticals, photographic chemicals and other compositions.

Japanese Patent Publication No. JP 2592732 B2 discloses a method of producing phenoxyethylamines by reacting, under base conditions, low molecular weight phenols and 2-oxazolidinone. Phenoxyethylamines are important raw materials for pharmaceuticals and pesticides.

German Patent Publication DE 19711004 A1 discloses the use of 2-oxazolidinone to prepare phenoxyaminoalkanes from low molecular weight phenols. 2-4-(Phenoxyphenoxy) ethylamine and ethyl 2-(Phenoxyphenoxy)ethylcarbamate are sequentially prepared in high yield and selectivity by the aminoethylation of 4-phenoxyphenol with 2-oxazolidinone under inert atmosphere, followed by amidation of 2-4-(Phenoxyphenoxy)ethylamine with carbonate derivatives.

Until now, the use of 2-oxazolidinone or a derivative thereof in aminoethylation transformations have been limited to low molecular weight phenols to produce phenoxyaminoalkanes. There has not been any teaching wherein 2-oxazolidinone or a derivative thereof has been used in aminoethylation transformations involving high molecular polyalkylphenols as in the case of the polyalkylphenoxyaminoalkanes disclosed in U.S. Pat. Nos. 5,669,939 and 5,851,242.

SUMMARY OF THE INVENTION

The present invention provides a novel process for the preparation of polyalkylphenoxyaminoalkanes which comprises the aminoethylation of a polyalkylphenol compound in the presence of a basic catalyst with 2-oxazolidinone or a derivative thereof having the following formula:

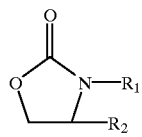

wherein $R_1$ and $R_2$ are independently hydrogen or lower alkyl having 1 to about 6 carbon atoms and wherein the polyalkyl group of said polyalkylphenol has an average molecular weight in the range of about 600 to 5,000.

The aminoethylation reaction of the present invention readily occurs using a basic catalyst selected from the group consisting of alkali metal lower alkoxides, alkali hydrides or alkali metal hydroxides in the temperature range of about 100° C. to 250° C., wherein the molar ratio of 2-oxazolidinone or a derivative thereof to polyalkylphenol compound is about 5:1 to 1:1 and wherein the number of equivalents of basic catalyst per equivalent of polyalkylphenol is about 0.05:1 to 1:1.

DETAILED DESCRIPTION OF THE INVENTION

As noted above, the present invention provides a novel process for the preparation of polyalkylphenoxyaminoalkanes which comprises an aminoethylation of a polyalkylphenol compound in the presence of a basic catalyst with 2-oxazolidinone or a derivative thereof having the following formula:

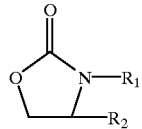

wherein $R_1$ and $R_2$ are independently hydrogen or lower alkyl having 1 to 6 carbon atoms and wherein the polyalkyl group of said polyalkylphenol has an average molecular weight in the range of about 600 to 5,000.

The reaction may be illustrated by the following:

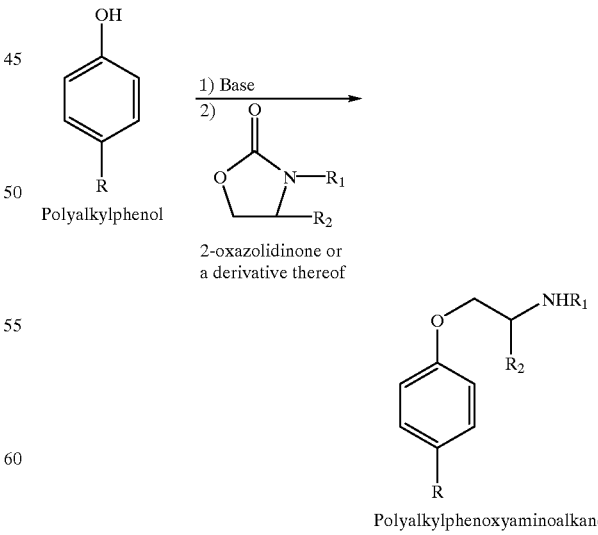

wherein R is a polyalkyl group having a molecular weight in the range of about 600 to 5,000, and $R_1$ and $R_2$ are as herein described.

3

Definitions

Prior to discussing the present invention in detail, the following terms will have the following meanings unless expressly stated to the contrary.

The term "alkyl" refers to both straight-and branched-chain alkyl groups.

The term "lower alkyl" refers to alkyl groups having 1 to about 6 carbon atoms and includes primary, secondary and tertiary alkyl groups. Typical lower alkyl groups include, for example, methyl, ethyl, n-propyl, isopropyl, n-butyl, sec-butyl, t-butyl, n-pentyl, n-hexyl and the like.

The term "polyalkyl" refers to an alkyl group which is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

Polyalkylphenoxyaminoalkanes may be prepared by the process of the present invention which comprises an aminoethylation of a polyalkylphenol compound with 2-oxazolidinone or a derivative thereof having the following formula:

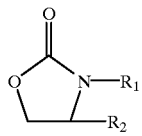

wherein $R_1$ and $R_2$ are defined herein, in the presence of a catalytic amount of an alkali metal lower alkoxide, alkali hydride or alkali metal hydroxide.

Polyalkylphenols are well known materials and are typically prepared by the alkylation of phenol with the desired polyolefin or chlorinated polyolefin. A further discussion of polyalkylphenols can be found, for example, in U.S. Pat. Nos. 4,744,921 and 5,300,701.

Accordingly, polyalkylphenols may be prepared from the corresponding olefins by conventional procedures. For example, polyalkylphenols may be prepared by reacting the appropriate olefin or olefin mixture with phenol in the presence of an alkylating catalyst at a temperature of from about 25° C. to 150° C., and preferably about 30° C. to 100° C. either neat or in an essentially inert solvent at atmospheric pressure. A preferred alkylating catalyst is boron trifluoride. Molar ratios of reactants may be used. Alternatively, molar excesses of phenol can be employed, i.e., about 2 to 3 equivalents of phenol for each equivalent of olefin with unreacted phenol recycled. The latter process maximizes monoalkylphenol. Examples of inert solvents include heptane, benzene, toluene, chlorobenzene and 250 thinner which is a mixture of aromatics, paraffins and naphthenes.

The polyalkyl group on the polyalkylphenols employed in the invention is generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

4

The preferred polyisobutenes used to prepare the presently employed polyalkylphenols are polyisobutenes which comprise at least about 20% of the more reactive methylvinylidene isomer, preferably at least about 50% and more preferably at least about 70%. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808. Such polyisobutenes, known as "reactive" polyisobutenes, yield high molecular weight alcohols in which the hydroxyl group is at or near the end of the hydrocarbon chain. Examples of suitable polyisobutenes having a high alkylvinylidene content include Ultravis 30, a polyisobutene having a number average molecular weight of about 1,300 and a methylvinylidene content of about 74%, and Ultravis 10, a polyisobutene having a number average molecular weight of about 950 and a methylvinylidene content of about 76%, both available from British Petroleum.

Typically, the polyalkyl group on the polyalkylphenol has a molecular weight in the range of about 600 to 5,000, preferably about 600 to 3,000, more preferably about 700 to 3,000, and most preferably about 900 to 2,500. The polyalkyl group on the polyalkylphenol may be in any position in the phenol ring. However, substitution at the para position is preferred.

As noted above, the polyalkylphenol compound is reacted with 2-oxazolidinone or a derivative thereof having the formula illustrated herein above, wherein $R_1$ and $R_2$ are independently hydrogen or lower alkyl having 1 to about 6 carbon atoms. Preferably, one of $R_1$ and $R_2$ is hydrogen or lower alkyl of 1 to about 4 carbon atoms, and the other is hydrogen. More preferably, one of $R_1$ and $R_2$ is hydrogen, methyl, or ethyl, and the other is hydrogen. Still more preferably, $R_1$ is hydrogen, methyl, or ethyl, and $R_2$ is hydrogen. Most preferably, both $R_1$ and $R_2$ are hydrogen. Examples of such compounds include, but are not limited to, 2-oxazolidinone, 3-methyl-2-oxazolidinone, 4-methyl-2-oxazolidinone, and 3-ethyl-2-oxazolidinone. The 2-oxazolidinone compound is preferred. These compounds are readily commercially available. For instance, 2-oxazolidinone and 3-methyl-2-oxazolidinone may be purchased from Aldrich Chemical Company. Alternatively, these compounds may be synthesized by conventional methods apparent to the skilled artisan.

The basic catalyst employed in the process of the present invention will generally be any of the well known basic catalyst selected from the group of alkali metal lower alkoxides, alkali hydrides or alkali metal hydroxides. Typical alkali metal lower alkoxides include, but are not limited to, sodium methoxide, potassium methoxide, sodium ethoxide, potassium ethoxide, sodium propoxide, potassium propoxide, sodium isopropoxide, potassium isopropoxide, sodium butoxide, potassium butoxide. Typically, the alkali metal lower alkoxides will contain 1 to about 6, preferably 1 to about 4, carbon atoms. Preferably, the alkali metal lower alkoxide is sodium methoxide. Sodium hydride and potassium hydride are typical alkali hydrides. Examples of alkali metal hydroxides include, but are not limited to, sodium hydroxide, lithium hydroxide, or potassium hydroxide. Sodium hydroxide and potassium hydroxide are preferred.

Typically, the reaction temperature for the aminoethylation reaction will be in the range of about 100° C. to 250°

C., and preferably in the range of about 130° C. to 210° C. The reaction pressure will generally be atmospheric or lower. Lower pressures may be used to facilitate the removal of carbon dioxide. Other carbon dioxide scavengers may be employed to facilitate the reaction, such as, for example, magnesium oxide or calcium oxide.

The molar ratio of 2-oxazolidinone or a derivative thereof to the polyalkylphenol compound is normally in the range of about 5:1 to 1:1, and preferably will be in the range of about 2:1 to 1:1. In general, the number of equivalents of the basic catalyst per equivalents of polyalkylphenol will be in the range of about 0.05:1 to 1:1, and preferably in the range of about 0.1:1 to 1:1.

The aminoethylation reaction may be carried out neat or in the presence of a solvent which is inert to the reaction of the polyalkylphenol compound and the 2-oxazolidinone or a derivative thereof. When employed, a typical solvent is an aromatic solvent such as Exxon 150 aromatic solvent, although other solvents apparent to those skilled in the art may also be used. For example, any number of ethers, aprotic polar solvents or alcohols may also be useful in the process of the present invention.

The aminoethylation reaction will generally be carried out over a period of about 2 to 24 hours, and preferably over a period of about 3 to 20 hours. Upon completion of the reaction, the desired polyalkyphenoxyaminoalkane is isolated using conventional techniques.

EXAMPLES

The invention will be further illustrated by the following examples, which set forth particularly advantageous process embodiments. While the Examples are provided to illustrate the present invention, they are not intended to limit it. This application is intended to cover those various changes and substitutions that may be made by those skilled in the art without departing from the spirit and scope of the appended claims.

Example 1

Preparation of

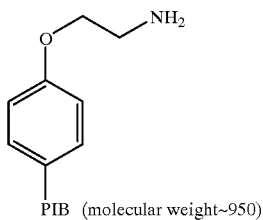

PIB (molecular weight~950)

Potassium hydroxide (assay 85%, 0.40 grams), Exxon Aromatic 150 solvent (35 mL) and 4-polyisobutyl phenol wherein the polyisobutyl group has an average molecular weight of about 950 (31.26 grams, prepared as in Example 1 of U.S. Pat. No. 5,300,701) were added to a flask equipped with a magnetic stirrer, Dean-Stark trap, reflux condenser, nitrogen inlet and thermometer. The reaction was heated at 170° C. until no more water came over. The Dean-Stark trap was removed and 2-oxazolidinone (2.61 grams) was added. The mixture was heated at 180° C. for 6 hours under enough vacuum to maintain a reflux. The reaction was cooled to room temperature, diluted with hexane, washed three times with water and once with brine. The organic layer was dried over anhydrous magnesium sulfate, filtered and the solvents removed in vacuo to yield a brown oil. The oil was chromatographed on silica gel, eluting with hexane:ethyl acetate (70:30) followed by hexane:diethyl ether:methanol:isopropylamine (40:40:15:5) to yield 22.77 grams of the desired product as a yellow oil. $^1$H NMR (CDCl$_3$) 7.25 (ABq, 2H), 6.8 (ABq, 2H), 4.0 (t, 2H), 3.1 (t, 2H), 2.35 (bs, 2H), 0.7–1.6 (m, 137H).

Example 2

Preparation of

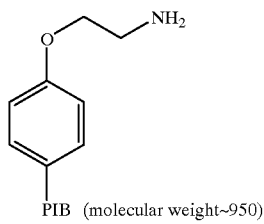

PIB (molecular weight~950)

Potassium hydroxide (assay 85% 1.46 grams), Exxon Aromatic 150 solvent (50 mL) and 4-polyisobutyl phenol wherein the polyisobutyl group has an average molecular weight of about 950 (20.8 grams, prepared as in Example 1 of U.S. Pat. No. 5,300,701) were added to a flask equipped with a magnetic stirrer, Dean-Stark trap, reflux condenser, nitrogen inlet and thermometer. The reaction was heated at 170° C. until no more water came over. The reaction was cooled to 150° C. The Dean-Stark trap was removed. Magnesium oxide (1.34 grams) and 2-oxazolidinone (1.92 grams) were added. The mixture was heated at 180° C. for 16 hours. The reaction was cooled to room temperature, diluted with hexane, filtered through Celite, washed three times with water and once with brine. The organic layer was dried over anhydrous magnesium sulfate, filtered and the solvents removed in vacuo to yield a brown oil. The oil was chromatographed on silica gel, eluting with hexane:ethyl acetate (70:30) followed by hexane:diethyl ether:methanol:isopropylamine (40:40:15:5) to yield 7.26 grams of the desired product as a yellow oil.

What is claimed is:

1. A process for the preparation of a polyalkylphenoxyaminoalkane which comprises the aminoethylation of a polyalkylphenol compound in the presence of a basic catalyst with 2-oxazolidinone or a derivative thereof having the following formula:

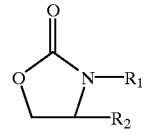

wherein R$_1$ and R$_2$ are independently hydrogen or lower alkyl having 1 to about 6 carbon atoms and wherein the polyalkyl group of said polyalkylphenol has an average molecular weight in the range of about 600 to 5,000.

2. The process according to claim 1, wherein the polyalkyl group has a molecular weight in the range of about 600 to 3,000.

3. The process according to claim 2, wherein the polyalkyl group has a molecular weight in the range of about 700 to 3,000.

4. The process according to claim 3, wherein the polyalkyl group has a molecular weight in the range of about 900 to 2,500.

5. The process according to claim 4, wherein the polyalkyl group is derived from polypropylene, polybutene, or a polyalphaolefin oligomer of 1-octene or 1-decene.

6. The process according to claim 5, wherein the polyalkyl group is derived from polyisobutene.

7. The process according to claim 6, wherein the polyisobutene contains at least about 20 wt % of a methylvinylidence isomer.

8. The process according to claim 1, wherein one of $R_1$ and $R_2$ is hydrogen or lower alkyl of 1 to about 4 carbon atoms, and the other is hydrogen.

9. The process according to claim 8, wherein one of $R_1$ and $R_2$ is hydrogen, methyl, or ethyl, and the other is hydrogen.

10. The process according to claim 9, wherein $R_1$ is hydrogen, methyl, or ethyl and $R_2$ is hydrogen.

11. The process according to claim 10, wherein both $R_1$ and $R_2$ are hydrogen.

12. The process according to claim 1, wherein the basic catalyst is selected from the group consisting of alkali metal lower alkoxide, alkali hydride or alkali metal hydroxide.

13. The process according to claim 12, wherein the alkali metal lower alkoxide is selected from the group consisting of sodium methoxide, potassium methoxide, sodium ethoxide, potassium ethoxide, sodium propoxide, potassium propoxide, sodium isopropoxide, potassium isopropoxide, sodium butoxide, potassium butoxide.

14. The process according to claim 13, wherein the alkali metal lower alkoxide is sodium methoxide.

15. The process according to claim 12, wherein the alkali hydride is sodium hydride or potassium hydride.

16. The process according to claim 12, wherein the alkali metal hydroxide is selected from the group consisting of sodium hydroxide, lithium hydroxide, or potassium hydroxide.

17. The process according to claim 16, wherein alkali metal hydroxide is sodium hydroxide or potassium hydroxide.

18. The process according to claim 1, wherein the aminoethylation temperature is in the range of about 100° C. to 250° C.

19. The process according to claim 17, wherein the aminoethylation temperature is in the range of about 130° C. to 210° C.

20. The process according to claim 1, wherein the molar ratio of 2-oxazolidinone or a derivative thereof to polyalkylphenol compound is about 5:1 to 1:1.

21. The process according to claim 19, wherein the molar ratio of 2-oxazolidinone or a derivative thereof to polyalkylphenol compound is about 2:1 to 1:1.

22. The process according to claim 1, wherein the number of equivalents of basic catalyst per equivalent of polyalkylphenol is about 0.05:1 to 1:1.

23. The process according to claim 21, wherein the number of equivalents of basic catalyst per equivalent of polyalkylphenol is about 0.1:1 to 1:1.

* * * * *